(12) United States Patent
Coker

(10) Patent No.: US 6,214,004 B1
(45) Date of Patent: Apr. 10, 2001

(54) VERTEBRAL TRIPLANER ALIGNMENT FACILITATOR

(76) Inventor: Wesley L. Coker, 601 Enquirer Ave., Nashville, TN (US) 37205

( * ) Notice: Subject to any disclaimer, the term of this patent is extended or adjusted under 35 U.S.C. 154(b) by 0 days.

(21) Appl. No.: 09/095,242

(22) Filed: Jun. 9, 1998

(51) Int. Cl.[7] .................................................. A61B 17/56
(52) U.S. Cl. ............................................. 606/61; 606/105
(58) Field of Search .................................. 606/61, 69, 70, 606/72, 73, 105

(56) References Cited

U.S. PATENT DOCUMENTS

| | | | | |
|---|---|---|---|---|
| 4,957,495 | * | 9/1990 | Kluger | 606/61 |
| 5,092,867 | * | 3/1992 | Harms et al. | 606/61 |
| 5,352,226 | * | 10/1994 | Lin | 606/61 |
| 5,363,841 | * | 11/1994 | Coker | 128/20 |
| 5,490,851 | * | 2/1996 | Nenov et al. | 606/61 |
| 5,667,506 | * | 9/1997 | Sutterlin | 606/61 |

* cited by examiner

Primary Examiner—Michael Buiz
Assistant Examiner—Julian W. Woo

(74) Attorney, Agent, or Firm—Waddey & Patterson; I. C. Waddey, Jr.

(57) ABSTRACT

This invention is a vertebral triplaner alignment facilitator to enable a surgeon to make minute vertebrae adjustments during spinal surgery. The vertebral triplaner alignment facilitator includes a support device which is adapted to support a tensioning device. The support device includes a support structure and a gurney. The gurney is adapted to support the tensioning device, while the support structure supports the gurney above a patient. The support structure typically includes a support rod, a sacral bridge, and adjustment rods. The support rod may be adapted to connect to a retractor. The sacral bridge may be adapted to sit on the iliac spines or crests of the pelvis. The adjustment rods movably engage the support rod and the sacral bridge such that the adjustment rods can move laterally over the patient and longitudinally relative to the retractor. A plurality of gurneys engage the adjustment rods such that they may move along the adjustment rods and may pivot about the adjustment rods. Each gurney tracks and pivots independently of the other gurneys, as does each adjustment rod. Each gurney is adapted to support the tensioning device such that the tensioning device may pivot about an axis perpendicular to the gurney. Thus, the alignment facilitator allows the tensioning device to be moved through multiple translational and to rotational degrees of freedom.

41 Claims, 6 Drawing Sheets

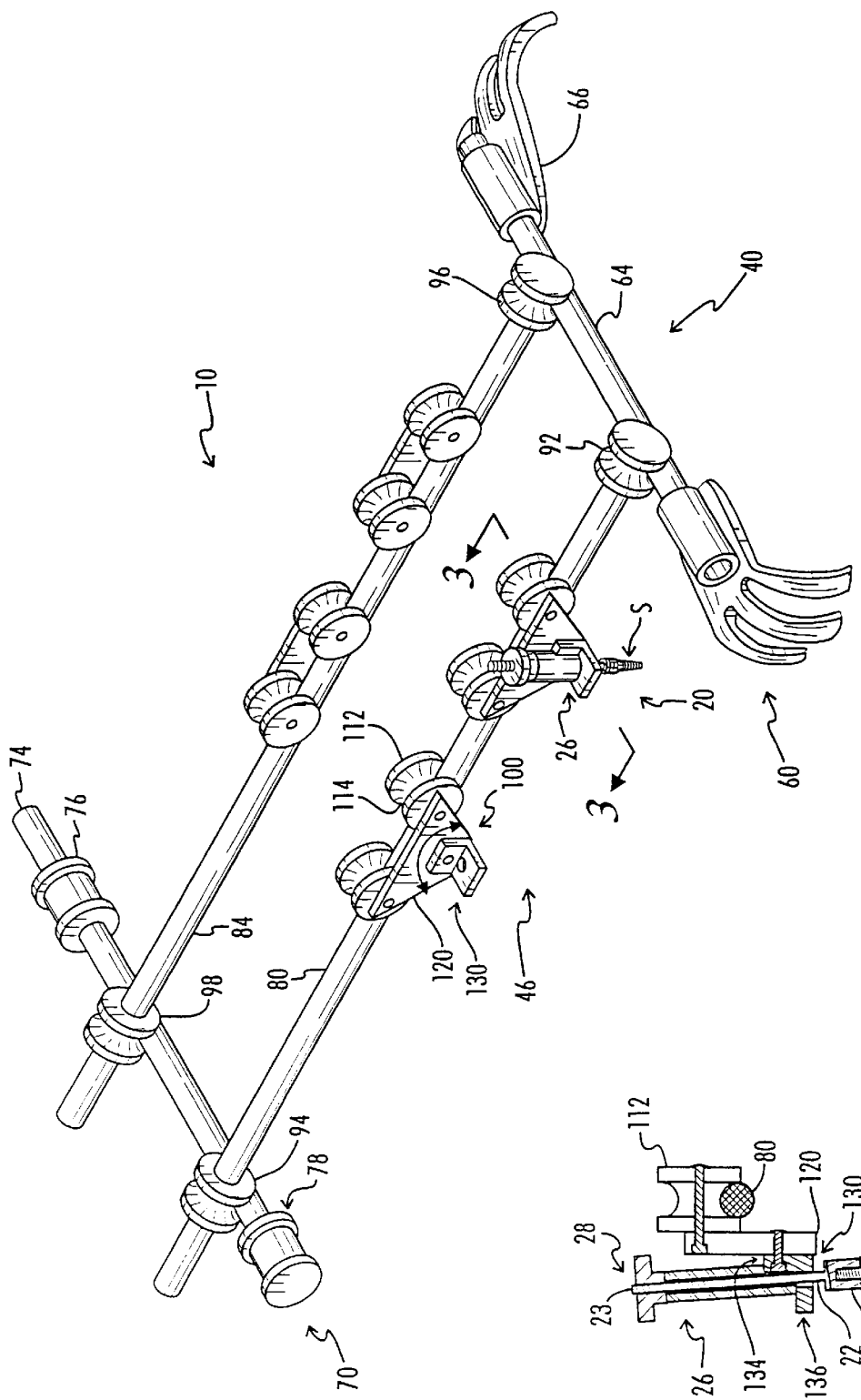
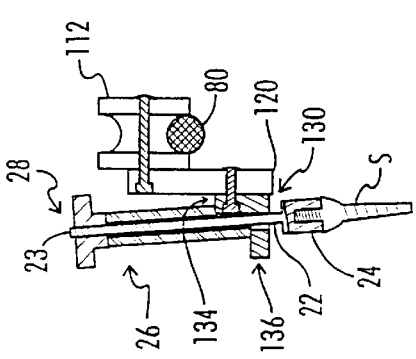
FIG. 2
FIG. 3

VERTEBRAL TRIPLANER ALIGNMENT FACILITATOR

BACKGROUND OF THE INVENTION

There are five bones in the human skeleton called vertebral bodies that comprise the structure of the lumbar spine. These bones are normally in a structure which allows them to be stacked on top of one another much like building blocks. In this relationship, and through their interlocking structure, the spine can bend forward, called flexion, or bend backwards, called extension. It can bend to either side, called lateral bending, and it can also twist or rotate. These ranges of motion are facilitated by muscles which attach to the lumbar vertebrae and these motions are stabilized not only by the bones themselves but by ligaments and discs which attach to these vertebrae.

In the course of human development, human deterioration and various disease processes and trauma, the alignment of the spine can be altered in such a way that one or more bones might become loose on one another causing an instability problem. The medical term for this problem is spondylolisthesis. The vertebral bodies also might develop a curvature problem called scoliosis. The development of arthritic spurs may also distort spinal configuration. Fractures, tumors, infections, and extensive surgical procedures can also distort spinal anatomy and spinal integrity resulting in the development of deformities of the lumbar spine.

In the last 30 years, a great deal of work has been done in orthopaedics on the development of procedures to stabilize deformity in the lumbar spine, and more recently to correct that deformity. The reason to correct the deformity is that the lumbar spine serves in many ways as a foundation on which the remaining structure of the thoracic and cervical spine exists. Having the lumbar spine in a more appropriate position allows for more normal functioning of the spinal structure above it.

Surgery is sometimes required to realign the spine. Generally, the surgeon will cut into the back of the patient to access the spine. He will use a retractor to hold skin and muscle away from the spine to improve his access to the spine. To align a lumbar vertebra, a screw called a pedicle screw will be inserted into the pedicle portion of a lumbar vertebra. Then the surgeon will pull on the pedicle screw to move the lumbar vertebra into appropriate alignment. Usually, internal hardware will then be attached to the spine to maintain proper alignment. To avoid trauma to the muscles, ligaments and nerves attached to the spinal cord, it is very important that the vertebra not be yanked into alignment. However, accomplishing this objective is easier said than done. Occasionally, with the pressure that is required to "pull" the vertebra into alignment, when the resistance to realignment is overcome, the surgeon cannot react quickly enough to prevent the vertebra from being yanked. In fact, gradual, even pressure on the vertebra is difficult to accomplish, thus making the surgery one of greater risk to complication than is desirable.

What is needed is a device to allow the surgeon access the pedicle screw from various angles and a platform and device which will enable the surgeon to apply even pressure on the vertebra as it is pulled into alignment without "yanking" the vertebra into place.

The device should be one which can be manipulated through multiple degrees of freedom to align with the pedicle screw is needed.

The device must enable the surgeon to apply a steady, gently, increasing tension to the pedicle screw during the alignment process.

The device should allow the surgeon to concentrate on the delicacies of the procedure, rather than muscling a vertebra into position.

The device should allow the surgeon to make minute adjustments to vertebra during spinal surgery to reduce the risk of back surgery to a patient.

Such a device would preferably maintain spinal alignment while the surgeon attaches in-dwelling hardware.

A device satisfying these needs is believed to be lacking in the prior art.

SUMMARY OF THE INVENTION

The invention relates to equipment used in conjunction with surgery and more specifically to a device for use in conjunction with back, or spine, surgery. The device enables the surgeon to make minute vertebral adjustments. This invention is an alignment facilitator which aids the orthopedic surgeon in realigning the vertebrae of the spine; it enables the surgeon to make minute vertebral adjustments during the course of spinal surgery and greatly reduces the risk associated with such a procedure.

During a lumbar vertebrae alignment procedure, the surgeon will attach a pedicle screw to the pedicle portion of lumbar vertebrae and gently pull vertebrae into alignment by applying tension to the pedicle screw. This invention includes a tensioning device adapted to attach to the pedicle screw and apply tension to the pedicle screw. It also includes a support device adapted to support the tensioning device over the patient. The support system includes an alignment system so that the surgeon can align the tensioning device with the pedicle screw. Alternatively, the support device may include a tracking and pivoting system which includes means for supporting and aligning the tensioning device.

The tracking and pivoting system will allow the surgeon to place the tensioning device in proper alignment with the pedicle screw. The support device will generally include a forward support and a rearward support for supporting the tracking and pivoting system.

The orientation and directions used in this application are relative to a patient lying face down. A forward location is closer to the head of the patient than a rearward location. Longitudinal and lateral directions are along the body of the patient, and across the body (from side to side), respectively. These directions and orientation would change as appropriate when the invention is used in other orientations. Other positions and orientations would allow the invention to be used to align other vertebrae or bones.

The rearward support, in one embodiment, includes a sacral bridge which is adapted to sit on iliac spines, or iliac crests of the patient. This is because the hip bones generally provide a solid stable surface which would not be traumatized by the, albeit relatively minimum, weight or pressure produced when tension is applied to the pedicle screw. The forward support, generally, includes a support rod. The support rod would be adapted to fit on a stable and strong surface, such as a retractor, or the scapula portion of the back, or similar surface.

The support device includes an adjustment rod slidably connected to the sacral bridge and slidably connected to the support rod so that the adjustment rod can move laterally above the patient. The adjustment rod may be movably connected to the support rod, so that the adjustment rod can move longitudinally relative to the support rod. Alternatively, or in combination, the support rod may be movably connected to the retractor so that the adjustment rod can move relative to the retractor.

The support device also includes a gurney for supporting and aligning the tensioning device. The gurney engages the adjustment rod so that the tensioning device may move longitudinally and may pivot about an axis parallel to the adjustment rod. In one embodiment, the gurney includes bearing connections at the forward and rearward supports so that the adjustment rod may pivot. Thus, the adjustment rod can move via the gurney, and the tensioning device may, but need not, be fixedly attached to the adjustment rod. Alternatively, the gurney can move via the adjustment rod.

Alternatively, the gurney includes a longitudinal pivotal connector engaging the adjustment rod so that the gurney may pivot or rotate about an axis parallel to the adjustment rod. In one embodiment the gurney pivots about the adjustment rod. In one embodiment, the tensioning device is movably attached to the gurney.

The gurney, in one embodiment, includes a slidable connector engaging the adjustment rod so that the gurney may move longitudinally along the adjustment rod. The slidable connector engaging the adjustment rod, in one set of embodiments, includes grooves, or slots, adapted to mate with slots in the adjustment rod. The slots may, alternatively, be in the forward and rearward supports to allow movement of the adjustment rod.

In another embodiment the slidable connector includes one or more guide rollers. Each guide roller, generally, includes a central groove for engaging the adjustment rod so that the guide roller may roll longitudinally along the adjustment rod and pivot about the adjustment rod. The guide roller need not have a central groove, it may, for instance, have a ball-bearing connector, or other connector, which allows similar movement.

The gurney further, typically, includes a second pivotal connector adapted to attach to the tensioning device so that the tensioning device may pivot about a second axis, where the second axis is transverse to the adjustment rod. Typically, the second axis will be perpendicular to the adjustment rod. The second axis may, however, be at some angle other then 90° relative to the adjustment rod. The tensioning device, however, must be sufficiently supported to allow tension to be applied to a pedicle screw.

In one embodiment, the gurney (or gurney assembly) typically includes guide rollers and a side plate. The side plate maintains the guide rollers in a fixed spatial relation relative to each other, and the guide rollers have a central groove.

The gurney assembly also typically includes a bracket pivotally connected to the side plate. The bracket is adapted to attach to the tensioning device so that the tensioning device may pivot about an axis perpendicular to the side plate.

In one embodiment, the bracket includes a first arm pivotally connected to the side plate and a second arm adapted to attach to the tensioning device so that the tensioning device may pivot by the axis perpendicular to the side plate. Since the axis perpendicular to the side plate is typically also perpendicular to the adjustment rod, the tensioning device will pivot about an axis perpendicular to the adjustment rod.

The gurney assembly, thus, provides the surgeon two translational degrees of freedom and two rotational degrees of freedom to align the tensioning device. In this embodiment, one translational degree of freedom is lateral translation through movement of the adjustment rod. The second translational degree of freedom is longitudinal through movement of the adjustment rod relative to the retractor, and movement of the gurney relative to the adjustment rod. The first rotational degree of freedom corresponds to rotation of the gurney about the adjustment rod. The second rotational degree of freedom corresponds to rotation of the bracket relative to the side plate of the gurney, i.e., about an axis perpendicular to the adjustment rod. It will be apparent to add hinged or pivotally connected members between the tensioning device and the gurney if one desires more flexibility or additional degrees of freedom.

The tensioning device is used in conjunction with the facilitator; it includes a means to attach the tensioning device to the pedicle screw and a means to apply tension to the pedicle screw. In one embodiment, the tensioning device includes a threaded connector having a threaded end and an attachment end; the attachment end is adapted to attach to the pedicle screw. The tensioning device also includes a collar and a tensioning knob. The collar receives the threaded end of the threaded connector and is disposed between the attachment end and the threaded end. The tensioning knob is threadably attached to the threaded end. Turning the tensioning knob draws the pedicle screw toward the tensioning device. Thus, small adjustments to the vertebrae are obtainable. Alternative conventional means for applying tension (or compression) will be apparent.

Although this invention is discussed with reference to a pedicle screw and lumbar vertebrae alignment, it will be apparent that the tensioning device may be adapted to attach to any alignment screw. For example, it may be adapted to attach to a vertebral laminar hook or an articular process screw, and the like. Similarly, the alignment facilitator may be used to facilitate alignment of cervical and thoracic vertebrae. It will also be apparent that the alignment facilitator may be used to align any two bones, or two pieces of a bone, with respect to each other. In that instance, rather than the tensioning device being adapted to attach to a pedicle screw, the tensioning device would be adapted to attach to whatever bone, or section of bone, is being aligned. The tensioning device may be attached to the bone or section of bone through use of screws, such as the pedicle screw, or through other conventional means. Thus, the alignment facilitator may be used to align fractured bones, out-of-joint knees, dislocated shoulders and rib, and the like. In general, the alignment facilitator may be adapted to aid an orthopedic surgeon apply smooth, steady tension to realign any two bones or vertebrae with respect to each other.

As such, this device has been developed to assist in the surgical treatment of correcting deformities of the lumbar spine though it is adaptable to other treatments. This correction process is generally aimed at dealing with the relationship of one or more vertebral bodies relative to one another:—in anterior/posterior translation (meaning front to back), side to side translation, axial compression or distraction (meaning top to bottom), and rotation.

Use of the triplaner vertebral alignment facilitator may include attaching the facilitator to the Coker Spinal Retractor, or similar device, on its more cephalad (toward the chest) use and attaching to a bridge between the two iliac crests on its more caudad (toward the pelvis) use. The invention, thus, floats on either side of the spine on a quarter inch rod. By means of the tracking and pivoting system, the device is attached to each of the involved vertebral bodies by a screw placed in the vertebral body's pedicle. The device can be fitted with a number of different connecting devices which makes it universally applicable to all pedicle screws produced in the U.S. and international markets. By tightening the tension on the attachment to the vertebral pedicle screw, this device facilitates the correction of the previously mentioned deformity (or deformities). Once the deformity is corrected, the device can be removed from one side of the spine and permanent spinal instrumentation can be installed and locked into place with appropriate locking devices. The alignment device is then removed from the opposite side of the spine and similar completion of the procedure is carried out on that side by application of the permanent instrumentation devices. The alignment device is then replaced by a permanently in-dwelling fixation system which connects two or more vertebral bodies in appropriate spinal alignment. This allows for a fusion between these bones to grow and thus maintain proper alignment of the bones.

An objective of this invention is to provide a surgeon with a device to make minute adjustments of the spine during spinal surgery, thus reducing the risk of trauma to the patient and speeding the patient's recovery. Another objective of the invention is to provide the surgeon with multiple angles from which to attach alignment screws; thus allowing the surgeon to optimally align the tensioning device with the alignment screw and the direction of alignment. This reduces off-alignment stress on the bone and improves the likelihood of achieving a proper bone alignment.

The added dexterous control the surgeon receives by using the alignment facilitator, rather than other cumbersome methods, will allow the surgeon to concentrate on the delicacies involved in the treatment, rather than on manhandling the vertebrae into alignment. Yet another objective of the invention is to provide the surgeon with a device to maintain proper alignment while permanent in-dwelling hardware is attached to the patient's bones. A further objective of the invention is to provide alternate means of aligning bones in addition to lumbar vertebrae.

BRIEF DESCRIPTION OF THE DRAWINGS

FIG. 2 is a perspective view of a vertebral triplaner alignment facilitator adapted for use with a retractor.

FIG. 3 shows a section view of the tensioning device shown in FIG. 2.

DESCRIPTION OF THE PREFERRED EMBODIMENTS

Figure 1:
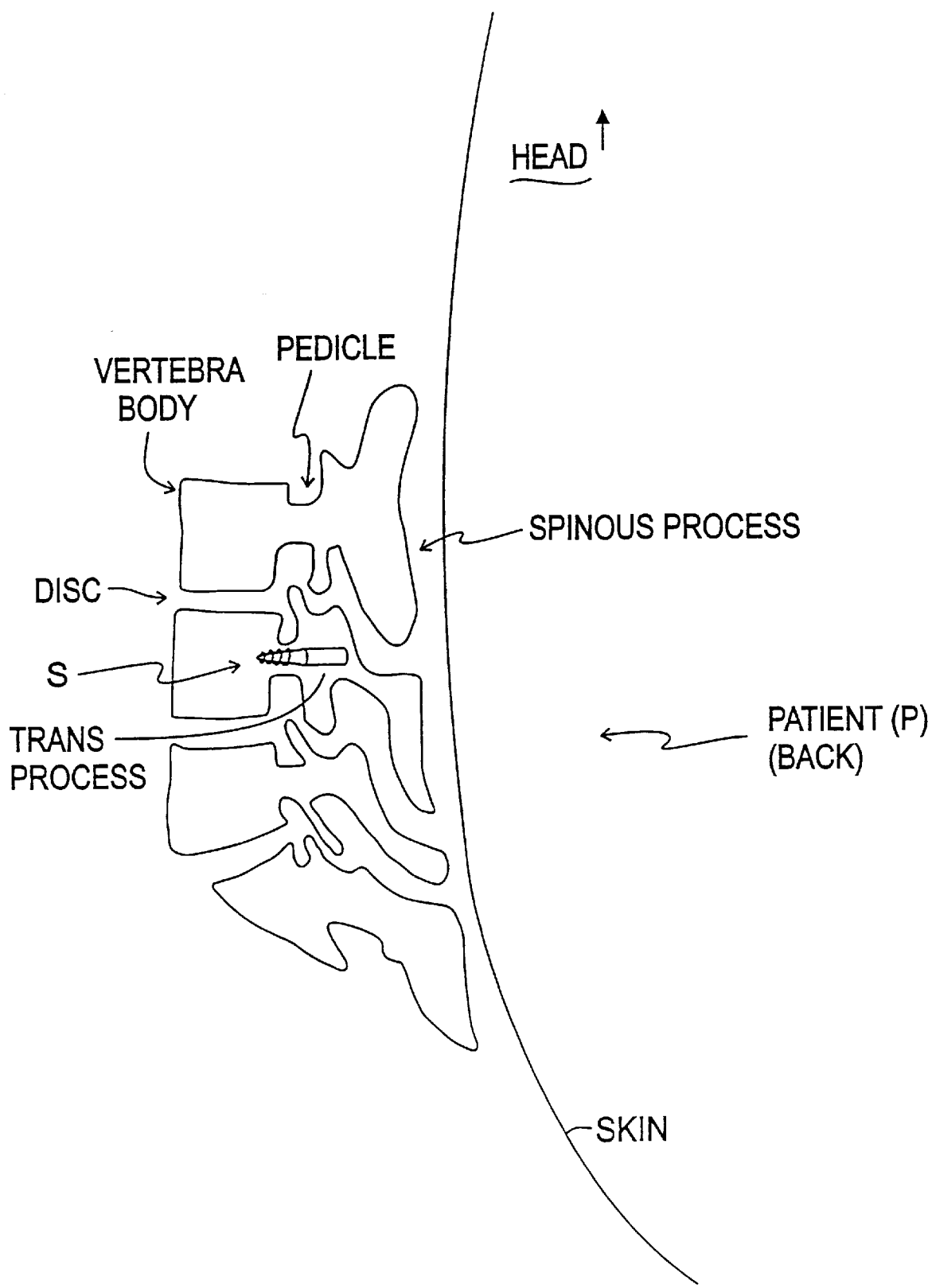
FIG. 1 shows a pedicle screw being used to align vertebrae within the lumbar section of the spine.

FIG. 1 shows a partial side view of a spine. A pedicle screw S is inserted into one of the lumbar vertebrae. The spine is realigned by pulling on the pedicle screw S. Typically, a surgeon will enter a patient's back to perform an alignment procedure. The surgeon will use a retractor to keep skin and muscle away from the spine to improve his access to the spine. The surgeon will need to get at the vertebrae from numerous angles. A screw is inserted into an appropriate portion of the vertebrae—typically a pedicle screw into the pedicle portion of the vertebra. The surgeon then applies tension to the pedicle screw S to pull the vertebra into proper alignment.

Figure 4:
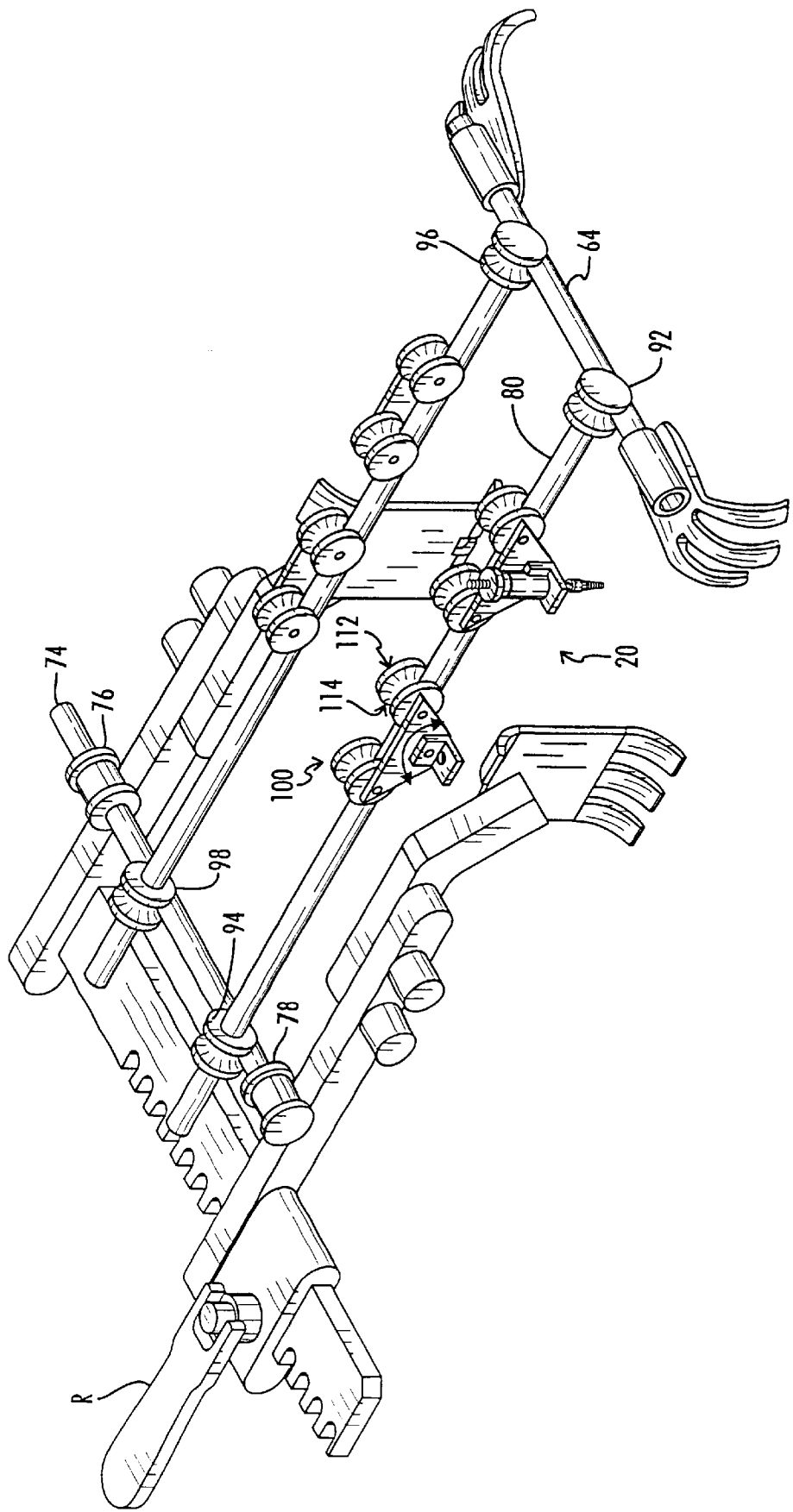
FIG. 4 is a perspective view of a vertebral triplaner alignment facilitator, similar to the one shown in FIG. 2, in use with a retractor.

FIG. 2 shows a triplaner vertebral alignment facilitator 10 adapted to be used with and supported by a retractor. FIG. 4 shows an alignment facilitator 10, substantially similar to the one shown in FIG. 2, engaging a retractor R. The retractor R is used to hold the skin and muscle away from the spine so that the surgeon can align the vertebrae by applying tension to the pedicle screw S inserted in the vertebrae. The details of construction of retractor R are shown in U.S. Pat. No. 5,363,841, Retractor For Spinal Surgery, issued Nov. 15, 1994, by Inventor Wesley L. Coker, which is incorporated herein by reference.

The triplaner vertebral alignment facilitator 10 shown in FIG. 2 includes a tensioning device 20 and a support device, or support means, generally denoted as 40, for supporting the tensioning device 20. The support device 40 includes an alignment means generally denoted as 46. The alignment means 46 may also be referred to as a tracking and pivoting system, or an alignment system. The alignment system 46 aligns the tensioning device 20 with the screw S. The alignment system 46 generally includes all the movable connections which allow the tensioning device 20 to pivot, rotate, and translate relative to a patient P. The movable connections will be described more fully with later discussion.

The support device 40 also includes a rearward support 60, and a forward support 70. The rearward support 60 and forward support 70 (also referred to as a support system, or support structure) support the alignment system 46. In the embodiment shown in FIG. 2, the rearward support 60 includes a sacral bridge 64; and the forward support 70 includes a support rod 74. The sacral bridge is adapted to set on iliac spines of the patient P. The support rod 74 shown in FIG. 2 is adapted to connect to the retractor R.

In the embodiment shown in FIG. 2, support rollers are attached to support rod 74 to rollably engage the retractor R. The support rollers include a first support roller 76 and a second support roller 78. An adjustment rod 80 movably engages the support rod 74 and the sacral bridge 64 so that the adjustment rod 80 can move laterally over the patient P. Adjustment rod 80 includes a first alignment roller 92 and a second alignment roller 94. The first alignment roller 92 rollably engages the sacral bridge 64, and the second alignment roller 94 slidably and rollably connects the adjustment rod 80 to the support rod 74 so that the adjustment rod 80 may slide in a first direction and roll and a second direction relative to the support rod 74. In the embodiment shown in FIG. 2, the first direction is longitudinal, and the second direction is lateral.

The triplaner alignment facilitator 10 shown in FIG. 2 includes a second adjustment rod 84 also movably engaging the support rod 74 and the sacral bridge 64 such that the second adjustment rod 84 can also move laterally over the patient P. The second adjustment rod 84 is similarly connected via its set of alignment rollers—first alignment roller 96 and second alignment roller 98. It will be apparent that a "rolling" or a "sliding" motion is not critical. The connection need not be "rollable" or "slidable," any antifriction connection, or other movable connection, e.g. ratcheting, would suffice.

The vertebral triplaner alignment facilitator 10 shown in FIG. 2, also includes a plurality of gurneys (gurney assemblies) 100 adapted to support the tensioning device 20.

Typically, each gurney 100 is substantially similar to the others. As such, only one gurney 100 will be described. The gurney 100 includes a plurality of guide rollers 112 engaging the adjustment rod 80. A side plate 120 maintains the guide rollers 112 in a fixed relation relative to each other such that the gurney 100 may roll longitudinally along the adjustment rod 80 and pivot about a first axis running through the adjustment rod 80.

Figure 9:
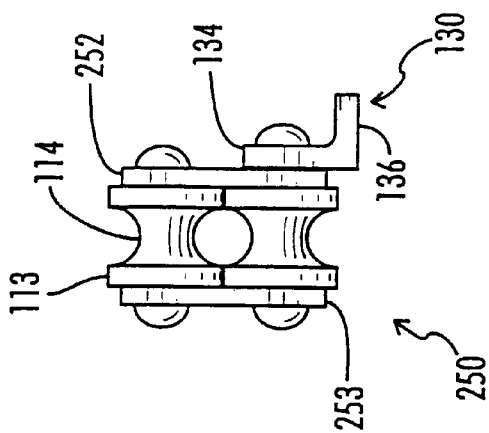
FIG. 9 is an end view of the gurney assembly.
Figure 8:
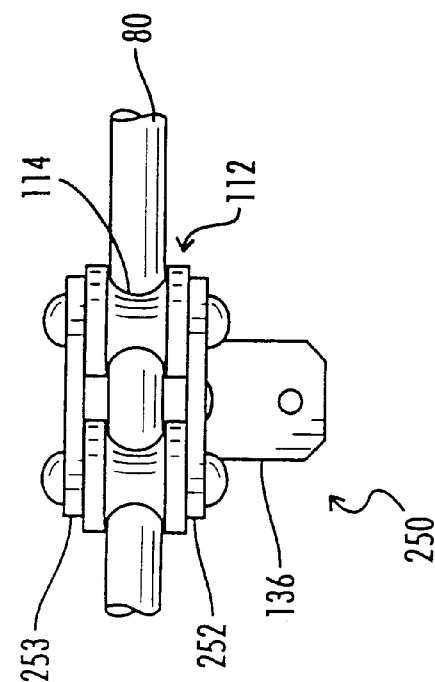
FIG. 8 is a top view of the gurney assembly.

FIG. 3 more clearly shows the guide roller 112 on the adjustment rod 80. Also shown in FIGS. 2 and 3 is a bracket 130 pivotally attached to the gurney 100. The bracket 130 includes a first arm 134, or a first end 134, pivotally attached to the side plate 120, and second arm 136, or another end 136. The second arm 136 is adapted to support the tensioning device 20 such that the tensioning device 20 may pivot about a second axis, where the second axis is perpendicular to the side plate 120. FIGS. 8 and 9 also show a bracket substantially similar to the one shown in FIGS. 2 and 3.

It will be apparent that the second axis which the tensioning device 20 pivots about need not be perpendicular to the side plate 120 and the adjustment rod 80. The second axis may be transverse to the adjustment rod (or the first axis), where transverse is defined as other than parallel. The first axis, which the tensioning device 20 typically pivots about, is generally parallel to the adjustment rod, but, it need not run through the adjustment rod 80. Further, the side plate 120 may be other than flat and need not be in plane with the adjustment rod 80. The gurney 100 may pivot about the one axis independent of pivoting about the other axis.

FIGS. 6 through 9 show a gurney 250 substantially similar to the gurney 100 shown in FIG. 2. The gurney 250 includes a side plate 252 maintaining the guide rollers 112 in a fixed relation, i.e. fixed relative to each other. Typically, the gurney 250 would include a second opposing side plate 253. FIG. 8 shows the second opposing side plate 253 attached to the guide rollers 112 on and the side plate 252 with pins. The guide rollers 112 are maintained between the two opposing side plates 252 and 253. The gurney 250 shown in FIG. 7 includes three guide rollers 112; at least two guide rollers 112 that are opposing. The opposing guide rollers engage the adjustment rod 80 and trap it between at least two guide rollers 112. The gurney 250 may move longitudinally relative to the adjustment rod 80 and pivot about the adjustment rod 80.

It will be apparent that the tensioning device 20 may be fixably connected to the adjustment rod 80 and the adjustment rod 80 movably connected to the forward and rearward supports.

Figure 10:
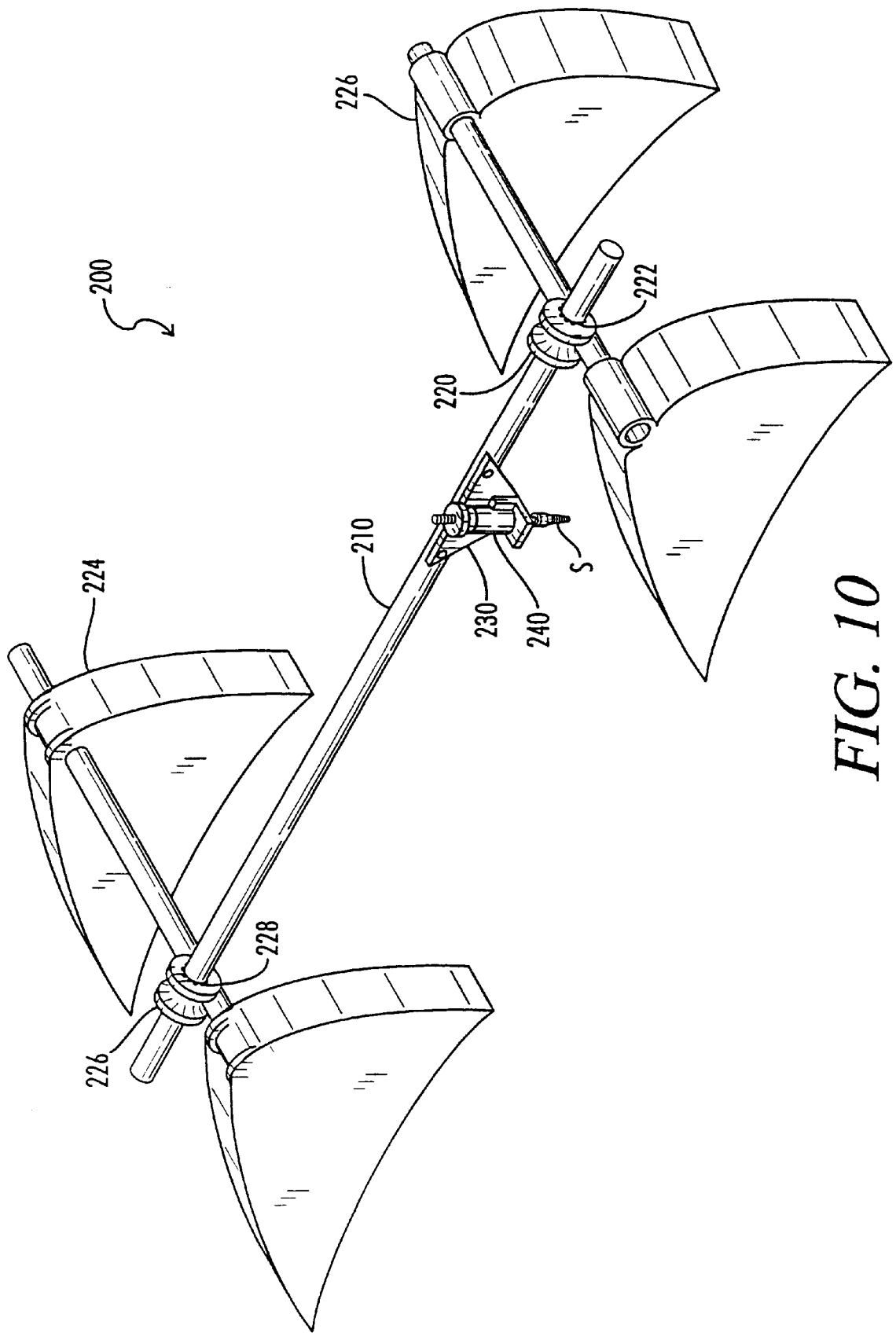
FIG. 10 shows a vertebral triplaner alignment facilitator with one adjustment rod and an alternate gurney from the one shown in FIG. 2.

FIG. 10 shows another embodiment of an alignment facilitator 200. The alignment facilitator 200 shown includes an adjustment rod 210 movably engaging a forward support 224, and a rearward support 226. The adjustment rod 210 engages the rearward support 226, and the forward support 224, through a first alignment roller 220, and a second alignment roller 226, respectively. The first and second alignment rollers 220 and 226 include roller bearings 222 and 228 to allow longitudinal movement of the adjustment rod 210 relative to the supports 224 and 226. The side plate 230 is fixedly attached to the adjustment rod 210. And the tensioning device 240 is pivotally attached to the side plate 230. The adjustment rod 210 and the alignment roller 220 and 226 may also be referred to as a gurney since they provide a moveable support for the tensioning device.

The assemblage shown in FIG. 10 provides support similar to the gurney 100 and adjustment rod 80 shown in FIG. 2. Both embodiments provide support while allowing pivoting of the tensioning device about an axis through to the adjustment rod, lateral movement of the adjustment rod, and longitudinal movement of the adjustment rod.

The single adjustment rod model may be used where multiple adjustment rods are not required. One or more tensioning devices may be supported on the adjustment rod. And the connections shown in FIG. 10 may be used with multiple adjustment rods and gurneys.

Referring back to FIG. 2, the guide rollers 112 shown include a central groove 114. The central groove 114 engages the adjustment rod 80 such that the gurney 100 may pivot about and roll along the adjustment rod 80. Gurneys, typically similar to gurney 100 previously described, also engage the second adjustment rod 84 as well as the first adjustment rod 80.

Sacral supports 66 are shown attached to the sacral bridge 60 in FIG. 2. It will be apparent that the sacral bridge 60 and the sacral supports 66 (as well as other supports) may be made adjustable to fit patients having different physical dimensions and limitations. Or the supports may be available in predetermined "sizes" to fit different patients. The sacral bridge 60 may also be a universal support structure adapted to support the alignment facilitator over other portions of the patient P. Similarly, the forward support 70 need not be adapted to connect to a retractor R. It may be adapted to attach to or rest on other portions of a patient P, or rest on other devices used during the procedure. (See FIG. 10.) The supports may be removably attachable supports and adapted to attach to particular locations on a patient or to meet needs of a particular patient.

FIG. 3 shows a sectional view of the tensioning device shown in FIG. 2 cut along section line A—A. FIG. 3 shows the adjustment rod 80, from an end view, supporting the guide roller 112. The side plate 120 is shown attached to the guide roller 112 and shown supporting the bracket 130. The bracket 130 shown includes a first arm 134 pivotally connected to the side plate 120 and a second arm 136. The second arm 136 supports the tensioning device 20.

The tensioning device 20 shown in FIG. 3 includes a threaded connector 22, a collar 26, and a tensioning knob 28. The threaded connector 22 shown includes an attachment end 24 and a threaded end 23. The collar 26 is disposed between the attachment end 24 and the threaded end 23. The tensioning knob 28 is threadably attached to the threaded end 23. Turning the tensioning knob 28 applies tension to the pedicle screw S and pulls the vertebrae into alignment.

Figure 5:
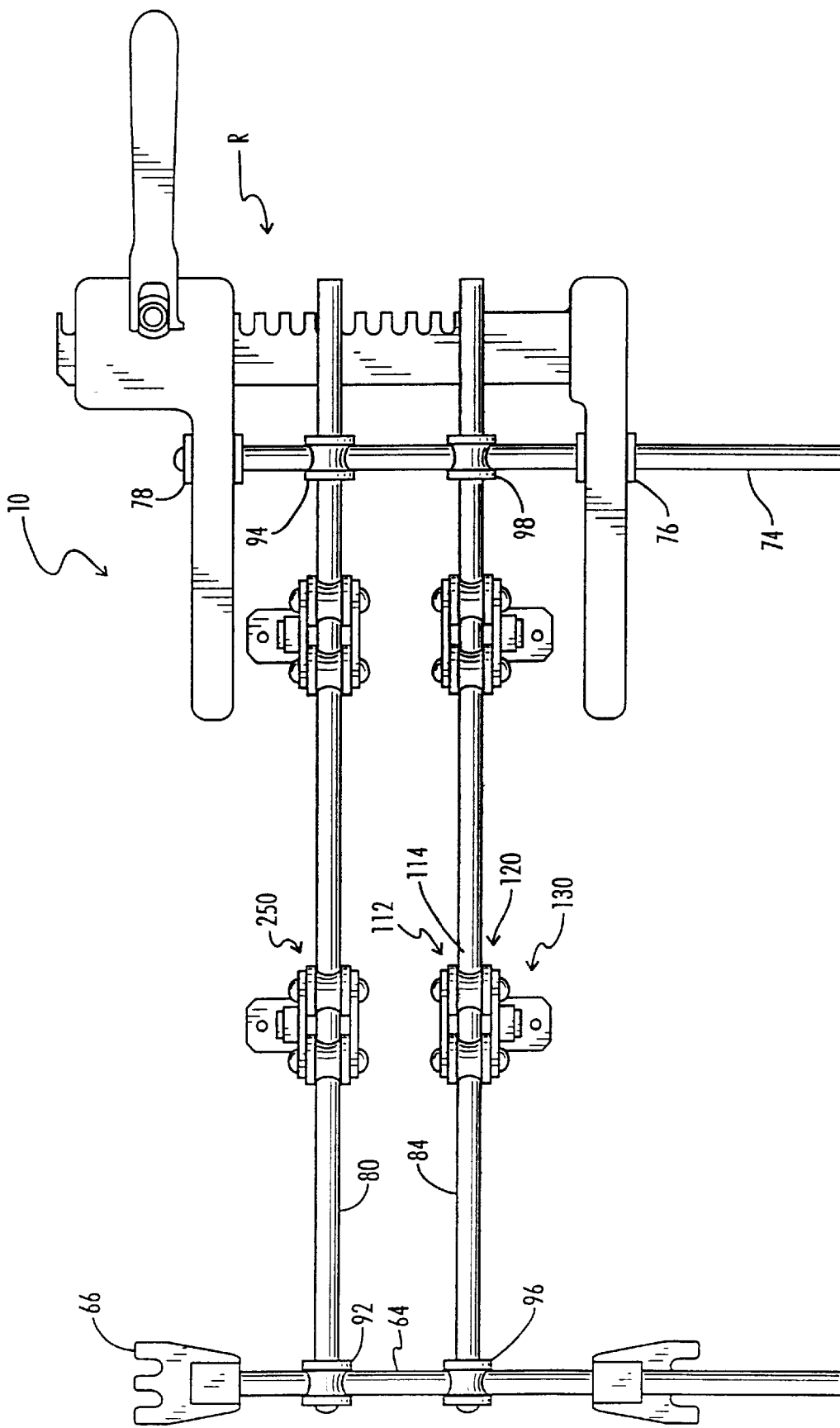
FIG. 5 shows a plan view of a vertebral triplaner alignment facilitator in use with a retractor.
Figure 6:
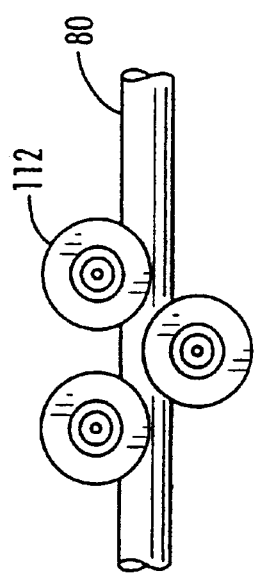
FIG. 6 shows a side view of a gurney assembly.
Figure 7:
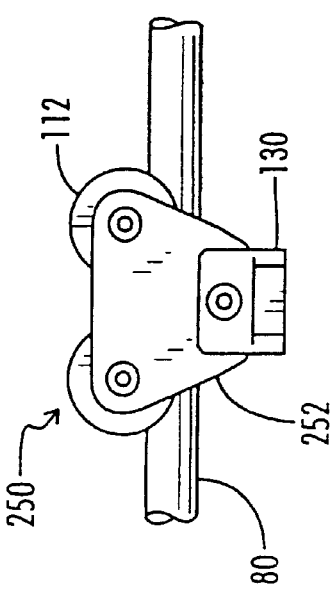
FIG. 7 shows a side view of a gurney assembly showing the guide rollers behind the side plate.

FIG. 5 shows a plan view of a vertebral triplaner alignment facilitator substantially similar to the one shown in FIG. 2. It is shown adapted for use with a retractor R. The retractor R is also shown. FIG. 6 shows a side view of a gurney assembly 250. FIG. 7 shows a side view of a gurney assembly 250; the side plate 252 has been removed to show the guide rollers 112. FIG. 8 is a top view of the gurney assembly 250. FIG. 9 is an end view of the gurney assembly 250. Side plate 252 and second opposing side plate 253 are shown in FIGS. 8 and 9 maintaining guide rollers 112 in a fixed relative position.

The guide rollers, alignment rollers, and other connections may be "loose" to provide free movement. Alternatively, they may be "tight" to provide restrained movement. Preferably, the connectors are in between "loose" and "tight" to provide firm connections which may be easily adjusted, but will prevent unintended slippage. Preferably, the gurney "floats" on adjustment rods 80 or 84 for ease of positioning. However, the guide rollers in one embodiment include a releasable ratchet mechanism to lock the guide roller down as the tensioning device distracts the bone.

In a preferred embodiment, similar to those shown in FIGS. 2 and 4, the vertebral triplaner alignment facilitator 10 includes a support device 40, the support device 40 adapted to support a tensioning device 20. The support device 40 includes a rearward support 60 and a forward support 70, and a gurney 100. The gurney 100 is adapted to support the tensioning device 20; and the forward and rearward supports 70 and 60 support an adjustment rod 80. The adjustment rod 80 supports the gurney 100 above a patient P, or relative to a patient. The forward support 70 includes a support rod 74. The rearward support 60 includes a sacral bridge 64. The support rod 74 is adapted to connect to a retractor R, and the sacral bridge 64 is adapted to sit on the iliac spines or crests of a patent P. The adjustment rod 80 movably engages the support rod 74 and the sacral bridge 64 such that the adjustment rod can move laterally over the patient P.

The vertebral triplaner facilitator 10 includes a second adjustment rod 84 similarly engaging the support rod 74 and the sacral bridge 64. The adjustment rods' engagement will be described for one adjustment rod, since, typically, the connections for the adjustment rods are similar. The adjustment rod 80 includes a first alignment roller 92 and a second alignment roller 94. The first alignment roller 92 rollably engages the sacral bridge 64. The second alignment roller 94 slidably and rollably connects the adjustment rod to the support rod 74 so that the adjustment rod 80 may move in a first direction (laterally) and may move in a second direction (longitudinally) relative to the support rod 74. The second adjustment rod 84 is similarly connected through a first alignment roller 96 and a second alignment roller 98.

A plurality of gurneys 100 engage the adjustment rods (80 and 84). Each gurney 100 tracks and pivots independently of the other gurneys. Likewise, each adjustment rod (80 or 84) moves independently of the other adjustment rod (84 or 80).

The gurney 100 will be described with respect to the adjustment rod on which it sits, or engages. The gurney 100 includes a plurality of guide rollers 112 engaging the adjustment rod 80, the plurality of guide rollers 112 including at least two opposing guide rollers such that the adjustment rod 80 is between the two opposing guide rollers 112. The opposing guide rollers 112 trap the adjustment rod 80 there between such that the gurney 100 may roll along, and pivot about, the adjustment rod 80.

Each guide roller 112 includes a central groove 114. The central groove engages the adjustment rod 80 such that the gurney 100 may roll longitudinally along the adjustment rod 80 and pivot about the adjustment rod 80. The gurney 100 also includes a side plate 120. The side plate 120 maintains the guide rollers 112 in a fixed relation relative to each other.

The gurney 100 includes a bracket 130. The bracket 130 includes a first arm 134 and a second arm 136. The first arm 134 is pivotally attached to the side plate 120 and the second arm 136 is adapted to support the tensioning device 20 such that the tensioning device 20 may pivot about an axis perpendicular to the side plate 120.

Thus, although there have been described particular embodiments of the present invention of a new and useful "Vertebral Triplaner Alignment Facilitator", it is not intended that such references be construed as limitations upon the scope of this invention except as set forth in the following claims. Further, although there have been described certain dimensions used in the preferred embodiment, it is not intended that such dimensions be construed as limitations upon the scope of this invention except as set forth in the following claims.

What is claimed is:

1. An alignment facilitator comprising:
   tensioning means for applying tension to a bone connection device; and
   support means for supporting the tensioning means over a patient, the support means including an alignment system connected to the tensioning means to align the tensioning means with the bone connection device, said alignment system comprising
      a glide roller such that the tensioning means may move longitudinally along the alignment system and may pivot about the alignment system and
      a support system supporting the alignment system relative to the patient.

2. A tensioning device for use in conjunction with a vertebral alignment facilitator, the tensioning device comprising:
   attachment means for attaching the tensioning device to a screw;
   a glide rolling device so that the tensioning means may move longitudinally about the facilitator and may pivot about the facilitator; and
   tensioning means, operably associated with the attachment means for applying tension to the screw.

3. The tensioning device of claim 2 wherein the attachment means comprises:
   a threaded connector having a threaded end and an attachment end, the attachment end adapted to attach to the screw;
   a collar for receiving the threaded end, where the collar is disposed between the attachment end and the threaded end; and
   a tensioning knob threadably attached to the threaded end.

4. A support device to support a tensioning device, where the tensioning device is adapted to apply tension to a screw in a patient, the support device comprising:
   an alignment means for aligning the tensioning device with the screw;
   a rearward support and a forward support for supporting the alignment means relative to the patient; and
   a tensioning device, the tensioning device including
      a threaded connector having a threaded end and an attachment end, the attachment end adapted to attach to the screw;
      a collar for receiving the threaded end, where the collar is disposed between the attachment end and the threaded end; and
      a tensioning knob threadably attached to the threaded end.

5. The support device of claim 4 wherein the rearward support comprises a sacral bridge adapted to sit on iliac spines.

6. The support device of claim 4 further comprising:
   the forward support including a support rod; and
   an adjustment rod movably connected to the rearward support and movably connected to the support rod so that the adjustment rod can move laterally relative to the patient.

7. The support device of claim 6 wherein the support rod is adapted to connect to a retractor.

8. The support device of claim 7 wherein the adjustment rod is movably connected to the support rod such that the adjustment rod can move longitudinally relative to the retractor.

9. The support device of claim 6 wherein the alignment means comprises a gurney engaging the adjustment rod so that the tensioning device may move longitudinally and may pivot about a first axis, the first axis parallel to the adjustment rod.

10. The support device of claim 9 wherein the gurney comprises a first pivotal connector engaging the adjustment rod so that the gurney may pivot about the adjustment rod.

11. The support device of claim 10 wherein the gurney further comprises a second pivotal connector adapted to attach to the tensioning device so that the tensioning device may pivot about a second axis, where the second axis is transverse to the adjustment rod.

12. The support device of claim 11 wherein the second axis is perpendicular to the adjustment rod.

13. The support device of claim 10 wherein the first pivotal connector comprises translation means for engaging the adjustment rod so that the gurney may move longitudinally relative to the adjustment rod.

14. The support device of claim 9 wherein the gurney comprises:
   a guide roller engaging the adjustment rod such that the gurney may move longitudinally along the adjustment rod and pivot about the adjustment rod; and
   a second pivotal connector adapted to attach to the tensioning device so that the tensioning device may pivot about a second axis transverse to the adjustment rod.

15. The support device of claim 14, the gurney further comprising:
   a side plate attached to the guide roller; and
   the second pivotal connector including a bracket, the bracket having a first arm and a second arm, the first arm pivotally connected to the side plate to pivot about the second axis, and the second arm adapted to support the tensioning device.

16. The support device of claim 15 wherein the second axis is parallel to the support rod.

17. The support device of claim 9 wherein the gurney comprises:
   a plurality of guide rollers including two opposing guide rollers, each guide roller having a central groove, the central groove engaging the adjustment rod, the adjustment rod maintained between the two opposing guide rollers so that the gurney may roll longitudinally along, and pivot about, the adjustment rod;
   a side plate attached to the guide rollers and securing each guide roller relative to the other guide rollers; and
   a bracket pivotally connected to the side plate, the bracket adapted to connect to the tensioning device so that the tensioning device may be pivoted about a second axis transverse to the adjustment rod.

18. The support of claim 9, wherein the gurney further comprises locking means for locking the pivoting device in position while the tensioning device is used to detract.

19. The support device of claim 4 wherein the alignment means further comprises:
   a first and a second adjustment rod, each adjustment rod movably connected to the rearward support and movably connected to the forward support so that the first and the second adjustment rods can move laterally and longitudinally relative to the patient; and
   at least one gurney engaging each adjustment rod, each gurney including tensioning device attachment means for attaching the tensioning device to a respective gurney, the respective gurney being the gurney to which the tensioning device may be attached.

20. The support device of claim 19, wherein each gurney comprises:
   a plurality of guide rollers, the plurality of guide rollers rollably and pivotally engaging a respective adjustment rod, the respective adjustment rod being the adjustment rod which the gurney engages;
   a side plate attached to the guide rollers and maintaining them in a fixed spatial relation relative to each other; and
   the tensioning device attachment means including a bracket pivotally connected to the side plate, the bracket adapted to attach to the tensioning device such that the tensioning device may pivot about an axis transverse to the respective adjustment rod.

21. The support device of claim 20 wherein the plurality of guide rollers comprise a first opposing guide roller and a second opposing guide roller, the first and second opposing guide rollers engaging the respective adjustment rod there between.

22. The support device of claim 21 wherein each guide roller includes a central groove engaging the respective adjustment rod.

23. The support device of claim 22 wherein the forward support is adapted to engage a retractor.

24. The support device of claim 23, further comprising:
   the forward support including a support roller adapted to engage the retractor so that the support rod may move longitudinally relative to the retractor; and
   the rearward support including a sacral bridge.

25. The support device of claim 24, further comprising a tension device attached to the bracket, the tensioning device including
   a threaded connector having a threaded end and an attachment end, the attachment end adapted to attach to the screw,
   a collar for receiving the threaded end, where the collar is disposed between the attachment end and the threaded end, and
   a tensioning knob threadably attached to the threaded end.

26. A vertebral triplanar alignment facilitator comprising:
   a tensioning device, the tensioning device including attachment means for attaching the tensioning device to a bone connection device, and tensioning means, operably associated with the attachment means for applying tension to the bone connection device;
   a support device supporting the tensioning device, the support device including a first gurney, the first gurney supporting the tensioning device;
   the support device further including a forward support, a rearward support, and a first adjustment rod movably engaging the forward support and the rearward support such that the first adjustment rod can move laterally relative to a patient, the first adjustment rod supporting the first gurney;
   the first gurney including two opposing guide rollers, the two opposing guide rollers engaging the adjustment rod such that the first adjustment rod is between the two opposing guide rollers;
   the first gurney further including a side plate connected to the two opposing guide rollers and maintaining them fixed relative to each other such that the first gurney may roll longitudinally along the first adjustment rod and may pivot about the first adjustment rod; and
   the first gurney further including a bracket having one end pivotally attached to the side plate and another end supporting the tensioning device such that the tensioning device may pivot about an axis transverse to the first adjustment rod.

27. The vertebral triplanar alignment facilitator of claim 26 wherein the support device further comprises:
  a second adjustment rod movably engaging the forward and the rearward supports such that the second adjustment rod can move laterally relative to the patient; and
  each adjustment rod including a first alignment roller and a second alignment roller, the first alignment roller movably engaging the rearward support, and the second alignment roller movably engaging forward support so that each adjustment rod may move longitudinally relative the forward support and move laterally relative to the rearward support.

28. The vertebral triplanar alignment facilitator of claim 27 wherein rearward support include a sacral bridge adapted to sit on iliac spines.

29. The vertebral triplanar alignment facilitator of claim 27 wherein the forward support is adapted to rollably engage a retractor.

30. The vertebral triplanar alignment facilitator of claim 27 wherein each guide roller includes a central groove, the central groove engaging the first adjustment rod.

31. The vertebral triplanar alignment facilitator of claim 26 wherein the support device further comprises a second gurney engaging the second adjustment rod.

32. An alignment facilitator comprising:
  an adjustment rod for supporting a tensioning device in proximity to a surgical incision in the back of a patient;
  a tensioning device supported on said adjustment rod and movable thereon; said tensioning device including:
    a connecting device for connecting the tensioning device to a pedicle screw implanted in a vertebrae of the patient; and
    a tensioning knob attached to the connecting device and adjustable in relation thereto whereby adjusting said tensioning knob applies tension to the screw.

33. The alignment facilitator of claim 32, wherein said connecting device comprises:
  a threaded connector having a threaded end and an attachment end, the attachment end adapted to the screw; and
  a collar for receiving the threaded end.

34. The alignment facilitator of claim 33, wherein the tensioning knob is threadably attached to the threaded end of the threaded connector.

35. The alignment facilitator of claim 32, wherein said alignment facilitator further comprises a forward support and a rearward support, wherein the adjustment rod is movably connected to the forward support and rearward support allowing the adjustment rod to move laterally relative to the patient.

36. The alignment facilitator of claim 35, wherein said support rod is adapted to connect to a retractor.

37. The alignment facilitator of claim 36, wherein the adjustment rod is movably connected to the forward support and rearward support such that the adjustment rod can move longitudinally relative to the retractor.

38. The alignment facilitator of claim 32, wherein said alignment facilitator comprises a plurality of tensioning devices supported on the adjustment rod.

39. The alignment facilitator of claim 32, wherein said tensioning device further comprises a glide roller device for movement along the adjustment rod.

40. The alignment facilitator of claim 39, wherein said glide roller comprises to opposing rollers, each roller having a central groove, the central groove engaging the adjustment rod, the adjustment rod maintained between the two opposing rollers so that the tensioning device may roll longitudinally along, and pivot about, the adjustment rod.

41. The alignment facilitator of claim 37, wherein said connecting device is attached to the tensioning device by a pivotally connected bracket so that the tensioning device may be pivoted about a second axis transverse to the adjustment rod.

* * * * *